(12) United States Patent
Andreoletti et al.

(10) Patent No.: US 8,221,520 B2
(45) Date of Patent: Jul. 17, 2012

(54) PRODUCTION OF THORIUM 228 STARTING FROM A NATURAL THORIUM SALT

(75) Inventors: Gilbert Andreoletti, Urville-Nacqueville (FR); Michel Belieres, Limoges (FR); Pascal Nardoux, Panazol (FR); Jean-Paul Moulin, Bois D' Arcy (FR); Anne Montaletang, Rilhac Rancon (FR); Patrick Bourdet, Bethesda, MD (US)

(73) Assignee: Areva NC, Paris (FR)

( * ) Notice: Subject to any disclaimer, the term of this patent is extended or adjusted under 35 U.S.C. 154(b) by 48 days.

(21) Appl. No.: 12/531,543

(22) PCT Filed: Mar. 18, 2008

(86) PCT No.: PCT/EP2008/053186
§ 371 (c)(1),
(2), (4) Date: Sep. 16, 2009

(87) PCT Pub. No.: WO2008/113792
PCT Pub. Date: Sep. 25, 2008

(65) Prior Publication Data
US 2010/0104467 A1    Apr. 29, 2010

Related U.S. Application Data

(60) Provisional application No. 60/911,390, filed on Apr. 12, 2007.

(30) Foreign Application Priority Data

Mar. 19, 2007   (FR) ..................................... 07 53909

(51) Int. Cl.
   *C22C 43/00*   (2006.01)

(52) U.S. Cl. .............................. 75/395; 75/394; 75/393

(58) Field of Classification Search ..................... 75/395, 75/394, 393
See application file for complete search history.

(56) References Cited

U.S. PATENT DOCUMENTS 4,423,007 A * 12/1983 Weir et al. ........................ 423/2
(Continued)

FOREIGN PATENT DOCUMENTS

AU          199727547 B2      1/1998
(Continued)

OTHER PUBLICATIONS

Hassfjell, et al., "The Development of the alpha-Particle Emiting Radionuclides 212-Bi and 213-Bi, and Their Decay Chain Related Radionuclides, for Therapeutic Applications", Chem. Rev. (2001) 101:2019-2036, no month.*

(Continued)

*Primary Examiner* — Jie Yang
(74) *Attorney, Agent, or Firm* — Oblon, Spivak, McClelland, Maier & Neustadt, L.L.P.

(57) ABSTRACT

The invention relates to a process for producing $^{228}$Th from a natural thorium salt, which comprises in succession: a) the separation of the radium from the other radioelements present in this salt, by at least one coprecipitation of the radium by barium sulphate, this coprecipitation comprising: i) the addition of sulphuric acid and a barium salt to an aqueous solution of said natural thorium salt in order to form a barium-radium sulphate coprecipitate and ii) the separation of the coprecipitate from the medium in which it has formed; b) the extraction of the thorium 228 coming from the decay of radium 228 from the coprecipitate thus separated; and, optionally c) the purification and concentration of the $^{228}$Th thus extracted. Applications: manufacture of radiopharmaceutical products useful in nuclear medicine, in particular in radioimmunotherapy for the treatment of cancers and AIDS.

25 Claims, 3 Drawing Sheets

U.S. PATENT DOCUMENTS

| | | | |
|---|---|---|---|
| 4,649,029 A * | 3/1987 | Nirdosh | 423/8 |
| 6,951,634 B2 * | 10/2005 | Tranter et al. | 423/2 |
| 2003/0166989 A1 * | 9/2003 | Larsen et al. | 600/1 |
| 2004/0028606 A1 | 2/2004 | Schwarz et al. | |
| 2010/0018347 A1 * | 1/2010 | Holden et al. | 75/394 |
| 2010/0113858 A1 * | 5/2010 | Vayr | 588/313 |

FOREIGN PATENT DOCUMENTS

| | | |
|---|---|---|
| CA | 1 145-487 | 4/1983 |
| EP | 0 014 553 | 8/1980 |
| FR | 2 750 414 | 1/1998 |
| JP | 60-65721 | 4/1985 |
| WO | WO 02/15943 A2 | 2/2002 |
| WO | WO 02/15943 A3 | 2/2002 |

OTHER PUBLICATIONS

Narbutt et al., "Gamma Emitting Radiotracers 224 Ra, 212 Pb, and 212 Bi from Natural Thorium", 1998, Appl. Radiat. Isot., vol. 49, Nos. 1-2, pp. 89-91.*

H. A. Doerner, et al., "Co-Precipitation of Radium and Barium Sulfates", Journal of the American Chemical Society, vol. 47, No. 3, 1925, pp. 662-675.

Louis Gordon, et al., "Coprecipitation of Radium with Barium Sulfate", Analytical Chemistry, vol. 29, No. 1, 1957, pp. 34-37.

Tieh-Chi Chu, et al., "Radioactive Disequilibrium of Uranium and Thorium Nuclide Series in Hot Spring and River Water from Peitou Hot Spring Basin in Taipei", Journal of Nuclear and Radiochemical Sciences, vol. 1, No. 1, 2000, pp. 5-10.

* cited by examiner

PRODUCTION OF THORIUM 228 STARTING FROM A NATURAL THORIUM SALT

CROSS-REFERENCE TO RELATED APPLICATIONS

This application is a 371 of PCT/EP08/053186 filed Mar. 18, 2008 and claims the benefit of U.S. provisional application 60/911,390 filed Apr. 12, 2007 and FR 07 53909 filed Mar. 19, 2007.

TECHNICAL FIELD

The present invention relates to a process for producing thorium 228 from a natural thorium salt.

This process, which allows high-purity thorium 228 to be obtained with very high yields, is especially applicable in the manufacture of radiopharmaceutical products useful in nuclear medicine, and in particular in radioimmunotherapy for the treatment of cancers or AIDS.

CONTEXT OF THE INVENTION

Radioimmunotherapy consists in irradiating cancerous cells present in an organism by injecting a pair composed of a monoclonal antibody or a peptide, onto which a radioelement emitting α or β particles is grafted and which can be selectively attached to these cancerous cells thanks to their specific antigens.

α-emitter radioimmunotherapy is intended more for the treatment of disseminated cancers, such as multiple myeloma, and for the treatment of micrometastases, whereas β-emitter radioimmunotherapy is intended more for the treatment of solid cancers measuring several millimeters in diameter and haematological cancers, such as lymphomas and leukaemias.

Certain descendants of thorium 228, in particular bismuth 212, which is an α-emitter, and lead 212, which is a β-emitter and the radioactive parent of bismuth 212, can be used in α-radioimmunotherapy especially for treating pancreatic cancers, or other peritoneal cancers and melanomas for which diseases α-radioimmunotherapy has undergone preclinical trials, in particular in the USA.

However, the preparation of radiopharmaceutical products comprising these descendants involves firstly being able to provide, and therefore to produce on an industrial scale, high-purity thorium 228.

Figure 1:
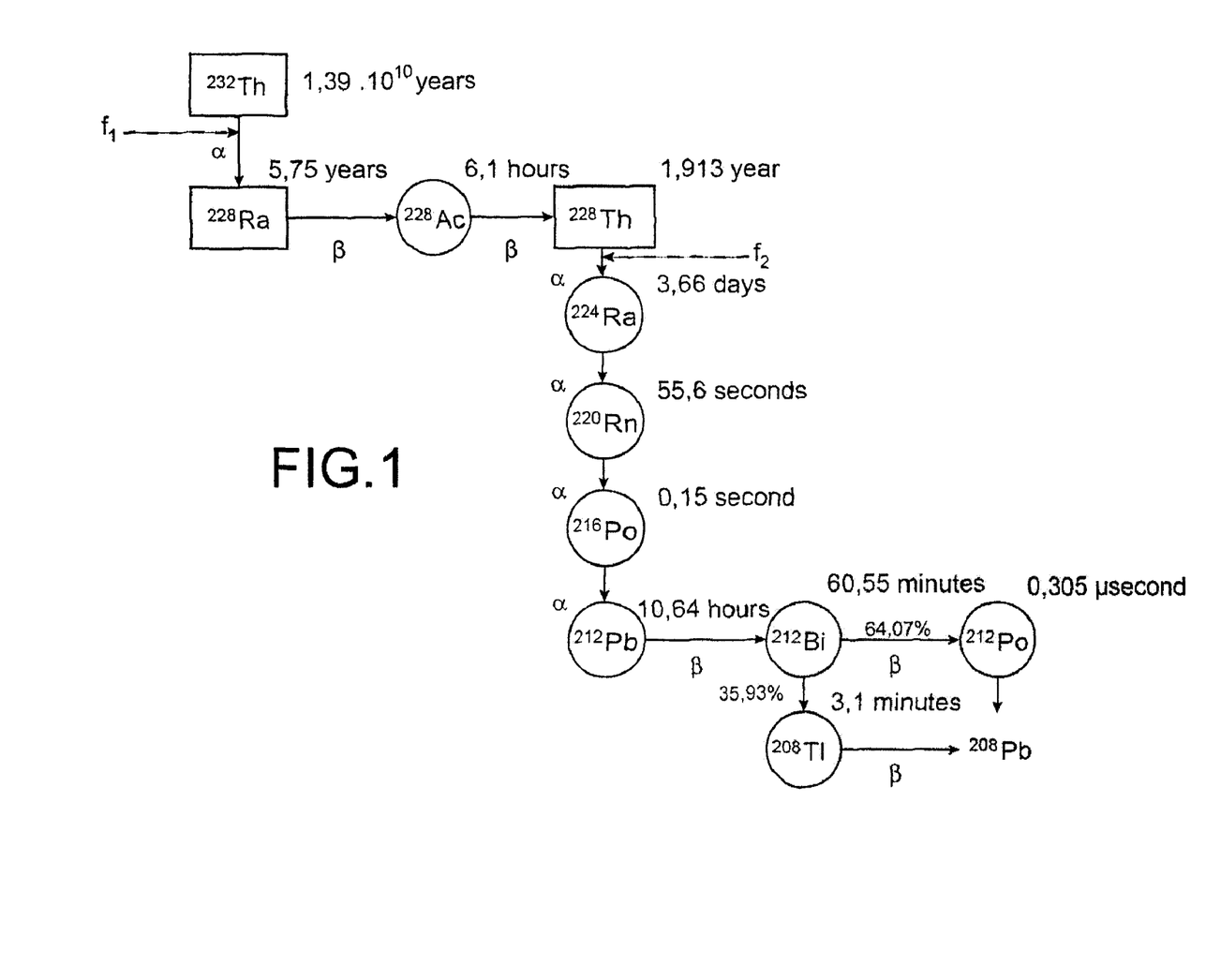
FIG. 1 shows the radioactive decay chain of thorium 232.

As illustrated in FIG. 1 appended herewith, which shows the radioactive decay of thorium 232, thorium 228 forms part of the radioactive family of thorium 232, which forms the major component of natural thorium extracted from ores such as monazite or thorite.

The inventors were therefore set the objective of developing a process for producing, from natural thorium, thorium 228 having a high degree of purity and with yields and costs compatible with an industrial exploitation.

SUMMARY OF THE INVENTION

This objective, and also others, have been achieved by the present invention, which proposes a process for producing thorium 228 from a natural thorium salt, which comprises in succession:

a) the separation of the radium ($^{224}$Ra and $^{228}$Ra) from the other radioelements present in this salt, by at least one coprecipitation of this radium by barium sulphate, this coprecipitation comprising:

i) the addition of sulphuric acid and a barium salt to an aqueous solution of said natural thorium salt in order to form a barium-radium sulphate coprecipitate and
  ii) the separation of the coprecipitate from the medium in which it has formed;

b) the extraction of the thorium 228 coming from the decay of radium 228 from the coprecipitate thus separated; and, optionally c) the purification and concentration of the thorium 228 thus extracted.

Thus, according to the invention, thorium 228 is produced from a natural thorium salt by trapping the radium present in this salt by coprecipitation with barium sulphate and by secondarily extracting, from the coprecipitate thus obtained, the thorium 228 coming from the decay of the radium that it contains, this extraction being optionally followed by a purification and a concentration of the thorium 228 extracted.

It should be noted that the coprecipitation of a radio-element, in particular radium, by barium sulphate is not novel per se. Thus, for example, its mechanisms have been studied by a number of authors such as H. A. Doerner and WM. M. Hoskins (*Journal of the American Chemical Society*, 47(3), 662-675, 1925) [1] and L. Gordon and K. Rowley (*Analytical Chemistry*, 29(1), 34-37, 1957) [2]. More recently, coprecipitation was used by T-C. Chu and J-J. Wang (*Journal of Nuclear and Radiochemical Sciences*, 1(1), 5-10, 2000) [3] for assessing the content of radium 226 of hot springs and river water from the Peitou basin in Taipei.

However, to the knowledge of the inventors, coprecipitation has never been proposed as a step of a process for producing thorium 228 from a natural thorium salt.

In addition, the way in which this coprecipitation is carried out in the prior art is clearly incompatible with the use to which it is put within the context of the process of the invention in which the aqueous solution of natural thorium salt that is subjected to the coprecipitation preferably has a salt concentration of 1 mol/l or higher and therefore has a very high saline load.

According to the invention, the natural thorium salt is preferably thorium nitrate, in which case the barium salt is itself preferably barium nitrate.

However, the natural thorium salt may for example also be thorium chloride, in which case the barium salt is then advantageously barium chloride.

Within the context of their work, the inventors have found that, to obtain yields close to 100%, both during radium coprecipitation and subsequent extraction of the thorium 228, it is necessary for the barium-radium sulphate particles that form during the coprecipitation to have a very fine particle size, that is to say in practice if possible a 50% particle size distribution of less than 10 µm by volume and less than 0.5 µm by number.

They have also found that barium-radium sulphate particles of such a particle size are obtained when, in substep i), the sulphuric acid and the barium salt are added to the aqueous thorium salt solution one after the other, and in this order, with stirring, and that this stirring is then maintained throughout the duration of particle formation.

Within the context of the invention, this is therefore the preferred way of proceeding.

Moreover, it has been found that the coprecipitation yields are also influenced by the ratio of sulphuric acid to barium salt, the formation of barium-radium sulphate particles being more favourable with an excess of sulphuric acid.

This is why the sulphuric acid is preferably added to the aqueous thorium salt solution in an amount chosen to be in excess relative to the barium salt, whereas the barium salt itself is preferably added in an amount chosen to be in deficit relative to the thorium salt.

To give an example, Ba/H$_2$SO$_4$ molar ratios ranging from 0.12 to 0.27 and Ba/Th molar ratios of around $2\times10^{-3}$ have proved to be perfectly suitable.

To reduce as far as possible the working volume of the equipment needed to implement the process of the invention, it is desirable to minimize the dilution effect produced by adding the sulphuric acid and the barium salt to the thorium salt solution.

It is therefore preferable to add the sulphuric acid in a highly concentrated form, ideally 36N, and the barium salt in a solid form, for example in the form of a powder.

After the coprecipitate has formed, it has to be separated from the medium in which it has formed.

The very small particle size of the coprecipitate, which is necessary for obtaining radium coprecipitation yields close to 100%, means that not any solid/liquid separation technique can be used to carry out this separation. In particular, this very low particle size would result in the filter medium becoming clogged if a simple dead-end filtration is used. Moreover, it is unnecessary to form a cake and to bring the coprecipitate to dryness. Keeping it settled or in suspension in a liquid is beneficial allowing for example, easier suspension operation in the subsequent steps of the process.

Various techniques can be used to obtain this result, such as for example:
the use of a cross-flow filtration membrane (for microfiltration or ultrafiltration), which promotes the permeation of the medium in which the coprecipitate has formed through the filter medium without the coprecipitate clogging the latter; or
the use of a flocculant for collecting the coprecipitate and sedimenting it, followed by removal of the supernatant resulting from this sedimentation.

Suitable flocculants are, for example, the low-charge anionic polyacrylamides sold by SNF Floerger.

According to a preferred way of implementing the process of the invention, this also includes, between steps a) and b), a step of washing the coprecipitate in order to decontaminate it of natural thorium, which step is advantageously carried out by bringing this coprecipitate into contact with a slightly acid aqueous solution, for example an aqueous nitric acid solution of about 0.5 normality.

Thus, if substep ii) is carried out by cross-flow filtration, a complementary diafiltration step, consisting in compensating for the rate of permeation through the filter medium by a liquid make-up in the feed, may advantageously be added so as to lower, as much as desired, the concentration of natural thorium of the medium under which the coprecipitate lies.

As a variant, when substep ii) is carried out by flocculating the coprecipitate and removing the resulting supernatant, the washing operation is advantageously carried out by repulping the coprecipitate several times by the slightly acid aqueous solution followed each time by decanting it.

According to another preferred way of implementing the process of the invention, and irrespective of the way in which substep ii) is carried out (flocculation or cross-flow filtration), the thorium 228 resulting from the decay of radium is extracted by bringing the coprecipitate into contact with a slightly acid aqueous solution.

As regards purification and concentration of the thorium 228 thus extracted, this is preferably carried out by ion exchange chromatography, and more especially by cation exchange, in which case the aqueous solution used to extract the thorium 228 is advantageously a slightly acid aqueous solution so that the thorium is in Th$^{4+}$ form, suitable for being attached to a cation exchanger, for example in the form of a resin or solvent. Here again, this slightly acid aqueous solution may especially be an aqueous nitric acid solution of about 0.5 normality.

According to one particularly preferred way of implementing the process of the invention, several successive coprecipitations are carried out in step a), these preferably being at least four coprecipitations, the inventors having indeed found that cumulative coprecipitation results in an increase in the rate of coprecipitation yield and consequently makes it possible to reduce the duration of step a), for equivalent yield, and the volume of the equipment.

These coprecipitations are advantageously carried out in the same reactor, in which case substep ii) is preferably carried out by sedimentation and removal of the resulting supernatant away from this reactor.

The process of the invention has, among other advantages, that of producing thorium 228 with a high degree of purity compatible with medical uses and requirements, that is to say producing pure thorium 228 without any radiological trace of the radioactive parents, and having no chemical impurity of foreign origin in a significant concentration, and therefore capable of being used for the manufacture of radio-pharmaceutical products intended for nuclear medicine.

The subject of the invention is therefore also the use of thorium 228 obtained by the process as defined above, for the preparation of radiopharmaceutical products intended for nuclear medicine, in particular for radioimmunotherapy and most particularly for α-radioimmunotherapy.

The invention will be more clearly understood in the light of the following examples, which refer to the appended figures.

Of course, these examples are given merely as illustrations of the subject matter of the invention and in no case constitute a limitation of this subject matter.

DETAILED DESCRIPTION OF THE INVENTION

EXAMPLE 1

Implementation of the Process of the Invention on an Industrial Scale

Figure 2:
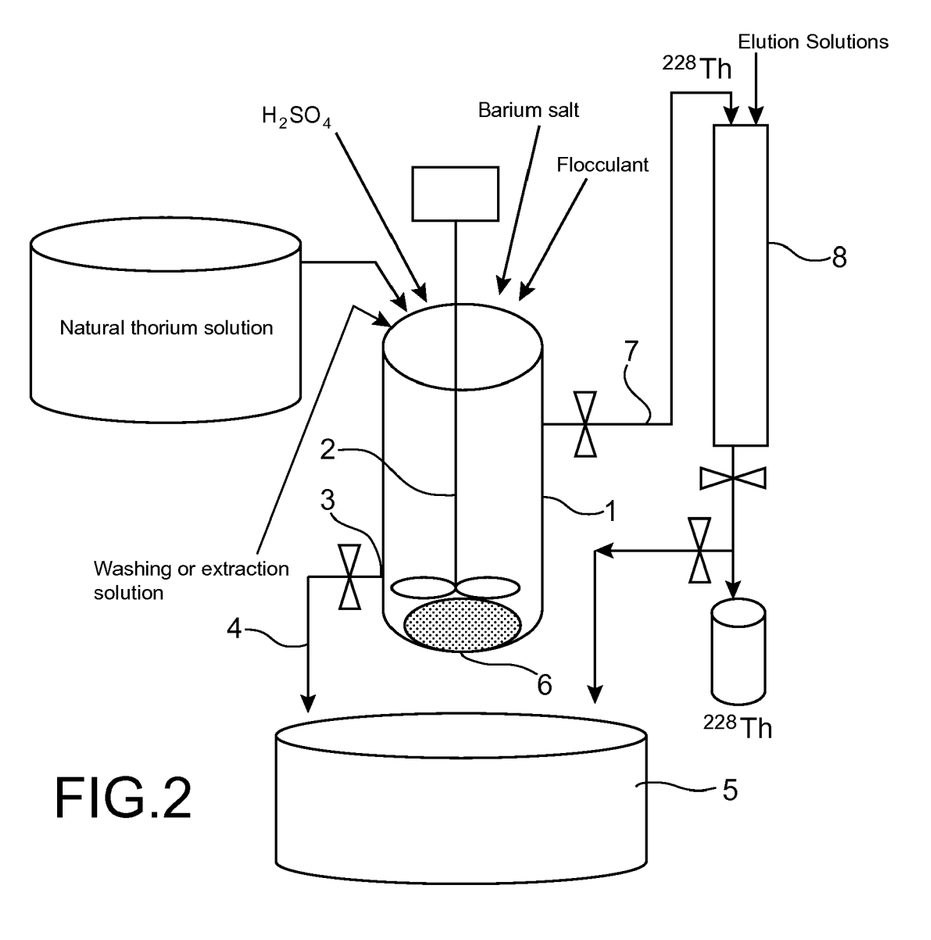
FIG. 2 shows a simplified diagram of one example of how the process of the invention is implemented on an industrial scale.

FIG. 2 shows schematically an example of how the process of the invention is implemented on an industrial scale.

In this example, the process comprises:
separation of the radium ($^{224}$Ra and $^{228}$Ra) present in a natural thorium salt from the other radioelements that are present therewith, by n coprecipitations with barium sulphate that are carried out in succession in the same reactor, each coprecipitation comprising the preparation of an aqueous solution of the thorium salt, the in situ formation of barium-radium sulphate, followed by flocculation of this coprecipitate and its separation from the supernatant;

washing of the floc thus obtained with a washing solution so as to remove the natural thorium present in the interstitial liquid of this floc;

extraction, from the floc thus washed, of the thorium 228 resulting from the decay of radium 228, with an extraction solution; and then purification and concentration of the thorium 228 thus extracted, by passage over an ion exchange resin.

All these operations are carried out at room temperature, that is to say at a temperature of 22±2° C.

1. Coprecipitations by Barium Sulphate

Each coprecipitation starts by introducing, into a reactor 1 fitted with a stirring system 2, an aqueous solution of a natural thorium salt, preferably with a concentration of 1 mol/l or higher, this solution being obtained beforehand by dissolving this salt, with stirring, in an appropriate volume of water.

The thorium salt is preferably thorium nitrate of high purity, i.e. ideally a purity of at least 99.8%, which is the case for example of the thorium nitrate available from Areva, N.C.

Next, each coprecipitation includes the in situ formation of barium-radium sulphate particles.

As indicated above, it is preferable for these particles to have a 50% particle size distribution ($D_{50}$) of less than 10 μm by volume and less than 0.5 μm by number, if it is desired to obtain yields close to 100%, both during coprecipitations and subsequent extraction of the thorium 228.

To do this, each coprecipitation includes introducing, into the reactor, with stirring, sulphuric acid followed immediately afterwards by a barium salt, for example barium nitrate, and maintaining the reaction mixture under this stirring for a time chosen before-hand according to the kinetics of coprecipitation and to the coprecipitation yield that it is desired to achieve with this kinetics.

The sulphuric acid must be present in the reaction mixture in excess relative to the barium salt. In contrast, the barium salt itself must be in deficit relative to the thorium salt. $Ba/H_2SO_4$ molar ratios of around 0.2 and Ba/Th ratios of around $2 \times 10^{-3}$ have for example given excellent results.

Moreover, the sulphuric acid is preferably introduced into the reactor 1 in a highly concentrated form, ideally 36N sulphuric acid, whereas the barium salt itself is preferably introduced into this reactor in a solid form, for example in the form of a powder, so as to minimize the dilution effect produced by adding these substances to the natural thorium salt solution and thus reduce as far as possible the working volume of the equipment needed to implement the process of the invention.

After the time allocated to the formation of the barium-radium sulphate particles, each coprecipitation comprises introducing a flocculant of the low-charge anionic polyacrylamide type, such as those sold by SNF Floerger, into the reactor and then stopping the stirring so as to allow the barium-radium sulphate particles to collect and settle on the bottom of the reactor.

What are thus obtained, after each coprecipitation, is a supernatant, which is removed from the reactor 1 by a draining system 3 and is directed, via a line 4, to a tank 5 provided for receiving the various residual effluent solutions generated by the process, and a floc which, itself, is retained in the reactor 1, until the end of the nth coprecipitation, and is therefore super-added, as from the second coprecipitation, to the floc resulting from the preceding coprecipitation.

What is finally obtained is a single floc 6 formed by the n flocs produced during the n coprecipitations.

2. Washing of the Floc and Extraction of the Thorium 228 from the Washed Floc

As illustrated in FIG. 2, the washing of the floc may be carried out in the reactor 1 by the addition of a washing solution, with stirring, followed by sedimentation of the floc and removal of the washing solution from the reactor, these operations being repeated one or more times.

Another possibility consists for example in collecting the floc in a column and in washing it by making the washing solution percolate through the floc.

It is also conceivable to carry out washing in combination with repulping of the floc in the reactor and purification over a resin, so as to remove the interstitial thorium 232.

The thorium 228 resulting from the decay of radium 228 may also be extracted by the addition of an extraction solution to the reactor 1, followed by sedimentation or by percolation of an extraction solution through the floc in a column.

The washing solution and the extraction solution are preferably weakly acid aqueous solutions, for example aqueous nitric acid solutions with a normality of about 0.5. This is because not only does a low acidity allow very effective purification of the natural thorium floc, followed by extraction of the thorium 228 therefrom with good yields, but it also allows the thorium 228 present in the effluent extraction solution to be in the cationic form $Th^{4+}$, which is propitious for subsequently attaching it onto a cation exchange resin in order to purify and concentrate it.

After the floc has been washed, the effluent washing solution is sent, via a line 4, to the tank 5, while the floc is retained in the reactor 1 and brought into contact with the extraction solution.

After the thorium 228 has been extracted, the effluent extraction solution, which is laden with this radio-element, is sent, via the line 7, to a purification/concentration device 8.

3. Purification and Concentration of the Thorium 228

As may be seen in FIG. 2, the device for purifying and concentrating the thorium 228 may consist of a column 8 prefilled with a cation exchange resin, preferably having an attachment acidity identical to that of the effluent extraction solution so that neither any addition of reactant, nor any dilution, is necessary in order for the thorium 228 to be attached to this resin. Suitable resins are for example available from Purolite.

The thorium 228 thus attached may then be easily eluted by varying the acidity so that it is in anionic form.

EXAMPLE 2

Experimental Validation

The example of how to implement the process of the invention described above was validated by laboratory trials, both as regards the dissolution of a thorium salt by the aqueous solution, and the coprecipitations with barium sulphate, the washing of the floc and the extraction of the thorium 228 from this floc.

1. Coprecipitations with Barium Sulphate

The trial consisted in carrying out ten successive coprecipitations, which will be called hereafter coprecipitations 1 to 10, in the same reactor.

Each of coprecipitations 1, 2, 4 to 6 and 8 to 10 was carried out by performing the following operations in sequence:

dissolution of 40 g of thorium nitrate (corresponding to 16 g of thorium) in 50 ml of water with magnetic stirring (bar magnet) at 750 revolutions/minute;

addition of 0.9 ml of $36NH_2SO_4$ ("Pro analysis", from Merck); followed, two minutes later by addition of 0.5 g of barium nitrate powder (NORMAPUR®, from Prolabo);

monitoring of the formation of barium-radium sulphate particles for 24 hours after the addition of barium nitrate (this addition representing t0) by:

removing specimens at t0+2 h, t0+6 h, t0+23 h and t0+24 h in order to measure the radiological activity and removing specimens at t0+23 h for analysing the particle size;

addition, at t0+24 h, of 2 ml of flocculant (FLOPAM® AH 912 SH, from SNF Floerger) dissolved in an amount of 0.2 g/l in water;

stopping the stirring and leaving the mixture to stand for 1 hour; and draining of the supernatant.

Coprecipitations 3 and 7 were carried out in the same way as described above, except that:

in the case of coprecipitation 3, the barium-radium sulphate particles were left to form for 96 hours so that the specimens intended for radio-logical activity measurements were removed at t0+2 h, t0+6 h, t0+95 h and t0+96 h, whereas the specimen intended for particle size analysis was removed at t0+95 h; and in the case of coprecipitation 7, the barium-radium sulphate grains were left to form for 72 hours so that the specimens intended for radiological activity measurements were removed at t0+2 h, t0+6 h, t0+71 h and t0+72 h, whereas the specimen intended for particle size analysis was removed at t0+71 h.

The specimens removed at t0+2 h, t0+6 h, t0+23 h, t0+71 h and t0+95 h were all filtered by means of a 0.1 μm Millipore® filter. Those taken at t0+24 h, t0+72 h and t0+96 h were all divided into two batches, namely batches that were filtered and batches that were not.

The radiological activities were determined by γ-spectroscopy on actinium 228 according to the NF M 60-790-6 standard. This method involves a delay time of at least four days between specimen removal and analysis, so as to "eliminate" the short-lived radio-elements (without their radioactive predecessor).

Coprecipitation of the radium by barium sulphate introduces two breaks in the radioactive decay chain of thorium: one between thorium 232 and radium 228 and the other between thorium 228 and radium 224. These breaks are shown symbolically by the respective arrows f1 and f2 in FIG. 1.

Thus, the actinium 228 analysed only derives from its predecessor, namely radium 228. It represents the unprecipitated radium, and its activity is in equilibrium with that of radium 228.

The coprecipitation yield is then calculated from this analysis as follows:

$$\rho = \frac{\text{(initial activity - analysed activity)}}{\text{initial activity}}.$$

The particle size analyses were carried out in liquid phase using a Malvern MASTERSIZER S instrument.

Table I below gives the activities of actinium 228, expressed in kBq/l, the coprecipitation yields, expressed as percentages, the $D_{50}$ values, expressed in μm, and the $D_{50}$ values by number, expressed in μm, which are obtained for each of the ten coprecipitations.

TABLE I

| Coprecipitation | Time t0 + h | Cumulative time in hours | [Ac228] × 50 kBq/l | Yield (%) | $D_{50}$ volume (μm) | $D_{50}$ number (μm) |
|---|---|---|---|---|---|---|
| 1 | 2 | 2 | 1.88 | 91.0 | | |
| | 6 | 6 | 0.70 | 96.6 | | |
| | 23 | 23 | 0.33 | 98.4 | 1.67 | 0.17 |
| | 24 (filtered) | 24 | 0.26 | 98.7 | | |
| | 24 (unfiltered) | 24 | 0.49 | 97.6 | | |
| 2 | 2 | 26 | 3.6 | 82.7 | | |
| | 6 | 30 | 1.93 | 90.7 | | |
| | 23 | 47 | 1.03 | 95.0 | 4.13 | 0.13 |
| | 24 (filtered) | 48 | 0.99 | 95.2 | | |
| | 24 (unfiltered) | 48 | 1.25 | 94.0 | | |
| 3 | 2 | 50 | 0.96 | 95.4 | | |
| | 6 | 54 | 0.47 | 97.7 | | |
| | 95 | 143 | 0.50 | 97.6 | 4.72 | 0.14 |
| | 96 (filtered) | 144 | 0.41 | 98.0 | | |
| | 96 (unfiltered) | 144 | 0.81 | 96.1 | | |
| 4 | 2 | 146 | 0.64 | 96.9 | | |
| | 6 | 150 | 0.38 | 98.2 | | |
| | 23 | 167 | 0.40 | 98.1 | 7.18 | 0.22 |
| | 24 (filtered) | 168 | 0.38 | 98.2 | | |
| | 24 (unfiltered) | 168 | 0.51 | 97.5 | | |
| 5 | 2 | 170 | 0.52 | 97.5 | | |
| | 6 | 174 | 0.38 | 98.2 | | |
| | 23 | 191 | 0.41 | 98.0 | 7.45 | 0.2 |
| | 24 (filtered) | 192 | 0.35 | 98.3 | | |
| | 24 (unfiltered) | 192 | 0.58 | 97.2 | | |
| 6 | 2 | 194 | 0.36 | 98.3 | | |
| | 6 | 198 | 0.39 | 98.1 | | |
| | 23 | 215 | 0.4 | 98.1 | 8.06 | 0.22 |
| | 24 (filtered) | 216 | 0.36 | 98.3 | | |
| | 24 (unfiltered) | 216 | 0.48 | 97.7 | | |
| 7 | 2 | 218 | 0.45 | 97.8 | | |
| | 6 | 222 | 0.48 | 97.7 | | |
| | 71 | 287 | 0.35 | 98.3 | 5.63 | 0.25 |
| | 72 (filtered) | 288 | 0.35 | 98.3 | | |
| | 72 (unfiltered) | 288 | 0.47 | 97.7 | | |
| 8 | 2 | 290 | 0.41 | 98.0 | | |
| | 6 | 294 | 0.46 | 97.8 | | |
| | 23 | 311 | 0.39 | 98.1 | 6.62 | 0.19 |
| | 24 (filtered) | 312 | 0.38 | 98.2 | | |
| | 24 (unfiltered) | 312 | 0.51 | 97.5 | | |
| 9 | 2 | 314 | 0.46 | 97.8 | | |
| | 6 | 318 | 0.44 | 97.9 | | |
| | 23 | 335 | 0.44 | 97.9 | 6.65 | 0.27 |
| | 24 (filtered) | 336 | 0.35 | 98.3 | | |
| | 24 (unfiltered) | 336 | 0.44 | 97.9 | | |

TABLE I-continued

| Coprecipitation | Time t0 + h | Cumulative time in hours | [Ac228] × 50 kBq/l | Yield (%) | $D_{50}$ volume (μm) | $D_{50}$ number (μm) |
|---|---|---|---|---|---|---|
| 10 | 2 | 338 | 0.4 | 98.1 | | |
| | 6 | 342 | 0.45 | 97.8 | | |
| | 23 | 359 | 0.44 | 97.9 | 6.84 | 0.13 |
| | 24 (filtered) | 360 | 0.35 | 98.3 | | |
| | 24 (unfiltered) | 360 | 0.41 | 98.0 | | |

This table shows that it is possible to obtain a coprecipitation yield of almost 98% at t0+24 h right from the first coprecipitation and this yield is not degraded when several coprecipitations are carried out in succession in the same reactor.

However, the table also shows that the kinetics of coprecipitation yield increases markedly after the 4th coprecipitation, since the yields reached at t0+2 hours for this coprecipitation and for the following ones are, respectively, 96.9%, 97.5%, 98.3%, 97.8%, 98.0%, 97.8% and 98.1%, whereas they are only 91.0%, 82.7% and 95.4% for the first three coprecipitations.

Thus, it is obviously beneficial, within the context of implementing the process of the invention on an industrial scale, to cumulate the coprecipitations so as to shorten their duration.

2. Washing the Floc

The floc obtained after the ten coprecipitations (volume: 3 ml) was introduced in a column 16 mm inside diameter (working volume: 16 ml), equipped with Wathman® 40 paper filters.

Next, a 0.5N aqueous nitric acid solution was made to run through this column, continuously and in an ascending direction, with a flow rate of 10 ml/h.

The elemental thorium concentration of the washing solution that leaves the column was analysed sequentially by inductively coupled plasma atomic emission spectroscopy.

Figure 3:
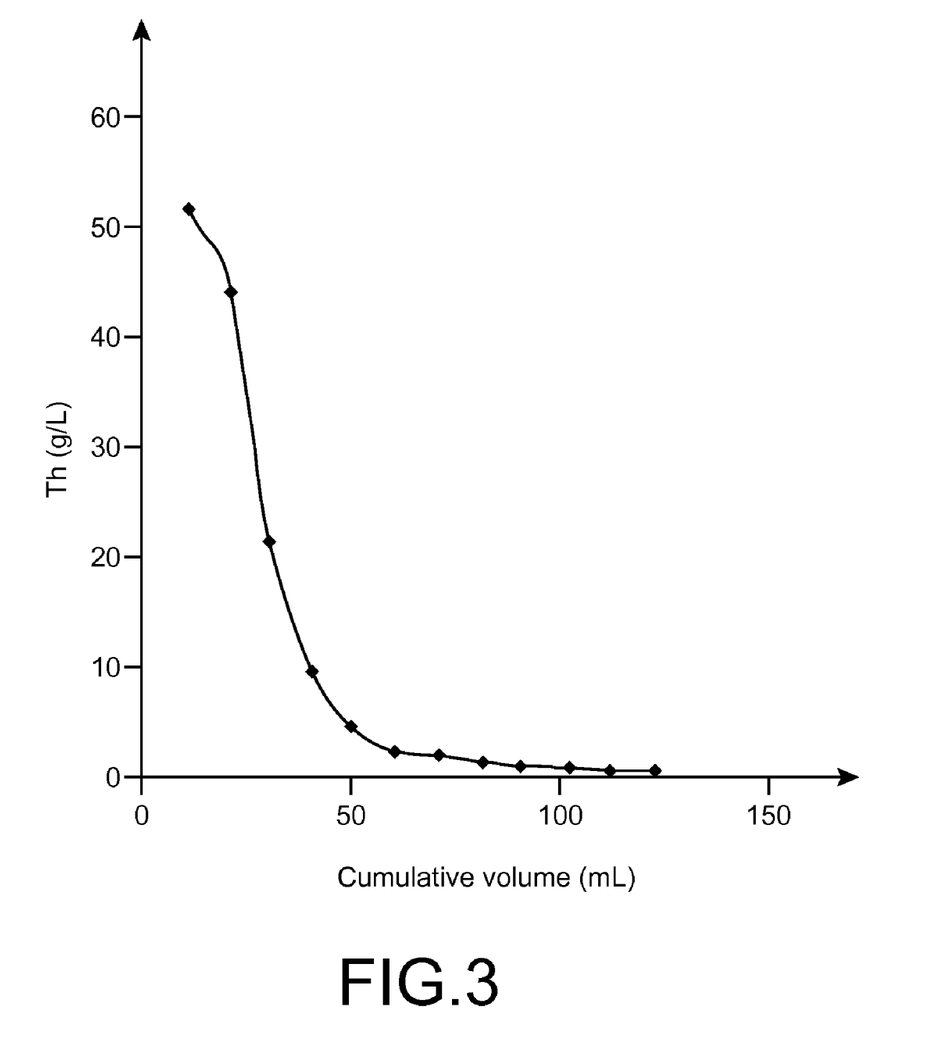
FIG. 3 shows the variation of elemental thorium concentration of an aqueous nitric solution that has been used for washing a floc obtained by the process of the invention as this washing proceeds.

As shown in FIG. 3, which plots the variation of this concentration, expressed in g/l, as a function of the cumulative volume of the washing solution, expressed in ml, the thorium present in the interstitial volume of the floc can be easily and completely eliminated by washing with a weakly concentrated aqueous nitric solution.

It should be noted that no degradation of the floc was observed during this washing.

3. Extraction of Thorium 228 from the Washed Floc

The washed floc was resuspended, with weak to moderate stirring, using a 0.5N aqueous nitric acid solution.

The thorium 228 formed was extracted using this solution. The extraction yield at 66 hours reached 100%.

References Cited

[1] H. A. Doerner and WM. M. Hoskins, *Journal of the American Chemical Society*, 47(3), 662-675, 1925.

[2] L. Gordon and K. Rowley, *Analytical Chemistry*, 29(1), 34-37, 1957.

[3] T-C. Chu and J-J. Wang, *Journal of Nuclear and Radiochemical Sciences*, 1(1), 5-10, 2000.

The invention claimed is:

1. A process for producing thorium 228 from a natural thorium salt comprising thorium 232 and decay products of thorium 232 including radium 228, radium 224 and other decay products, comprising in succession:

a) separating radium 228 and radium 224 from thorium 232 and the other decay products present in the salt, by at least one coprecipitating radium 228 and radium 224 by a barium sulphate, wherein said coprecipitating comprises:

i) adding a sulphuric acid and a barium salt to an aqueous solution of said natural thorium salt in order to form a medium comprising a barium-(radium 228 and radium 224) sulphate coprecipitate and a supernatant, and ii) separating the coprecipitate from the supernatant;

b) extracting from the coprecipitate thorium 228 coming from the decay of radium 228 thereby producing thorium 228.

2. The process according to claim 1, wherein the natural thorium salt is a thorium nitrate.

3. The process according to claim 1, wherein the barium salt is a barium nitrate.

4. The process according to claim 1, wherein the aqueous thorium salt solution has a thorium salt concentration of at least 1 mol/l.

5. The process according to claim 1, wherein the sulphuric acid and the barium salt are added to the aqueous thorium salt solution one after another and in this order, with a stirring, and the stirring is maintained throughout the coprecipitate formation.

6. The process according to claim 1, wherein the sulphuric acid is added to the aqueous thorium salt solution in an amount in excess relative to the barium salt.

7. The process according to claim 1, wherein the barium salt is added to the aqueous thorium salt solution in an amount in deficit relative to the thorium salt.

8. The process according to claim 1, wherein the sulphuric acid is 36N sulphuric acid.

9. The process according to claim 1, wherein the barium salt is in a solid form.

10. The process according to claim 1, wherein ii) comprises cross-flow filtrating the medium.

11. The process according to claim 10, further comprising, between a) and b), washing the coprecipitate.

12. The process according to claim 11, wherein ii) comprises cross-flow filtrating and diafiltrating the medium.

13. The process according to claim 1, wherein ii) comprises flocculating the coprecipitate and removing the supernatant.

14. The process according to claim 13, wherein flocculating the coprecipitate comprises adding a flocculant to the medium.

15. The process according to claim 1, further comprising, between a) and b), washing the coprecipitate.

16. The process according to claim 15, wherein washing the coprecipitate comprises bringing the coprecipitate into contact with a weakly acid aqueous solution.

17. The process according to claim 15, wherein washing the coprecipitate comprises at least one repulping the coprecipitate in a weakly acid aqueous solution, the repulping being followed by sedimenting the coprecipitate.

18. The process according to claim 1, wherein, in b), extracting thorium 228 comprises bringing the coprecipitate into contact with a weakly acid aqueous solution.

19. The process according to claim 1, wherein a) comprises successive coprecipitatings.

20. The process according to claim 19, wherein the successive coprecipitatings are carried out in the same reactor and ii) comprises flocculating the coprecipitate and removing the supernatant away from the reactor.

21. A process for manufacturing a radiopharmaceutical product for nuclear medicine, comprising implementing the process according to claim 1.

22. The process according to claim 21, in which the radiopharmaceutical product is for radioimmunotherapy.

23. The process according to claim 1, further comprising, after b), purifying and concentrating thorium 228 extracted.

24. The process according to claim 23, wherein, in c), purifying and concentrating thorium 228 comprises an ion exchange chromatography.

25. A process for producing thorium 228 from a natural thorium salt comprising thorium 232 and decay products of thorium 232 including radium 228, radium 224 and other decay products, and wherein the natural thorium salt has a purity of at least 99.8%, comprising in succession:
  a) separating radium 228 and radium 224 from thorium 232 and the other decay products present in the salt, by at least one coprecipitating radium 228 and radium 224 by a barium sulphate, wherein said coprecipitating comprises:
    i) adding a sulphuric acid and a barium salt to an aqueous solution of said natural thorium salt in order to form a medium comprising a barium-(radium 228 and radium 224) sulphate coprecipitate and a supernatant, and
    ii) separating the coprecipitate from the supernatant;
  b) extracting from the coprecipitate thorium 228 coming from the decay of radium 228 thereby producing thorium 228.

* * * * *